(12) United States Patent
Eichler

(10) Patent No.: US 10,631,909 B2
(45) Date of Patent: Apr. 28, 2020

(54) OPHTHALMIC SURGICAL CONTROL APPARATUS

(71) Applicant: Carl Zeiss Meditec AG, Jena (DE)

(72) Inventor: Michael Eichler, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 646 days.

(21) Appl. No.: 14/229,743

(22) Filed: Mar. 28, 2014

(65) Prior Publication Data

US 2014/0214024 A1 Jul. 31, 2014

Related U.S. Application Data

(63) Continuation of application No. PCT/EP2012/068767, filed on Sep. 24, 2012.

(30) Foreign Application Priority Data

Sep. 30, 2011 (DE) .................. 10 2011 114 584

(51) Int. Cl.
*A61B 18/00* (2006.01)
*A61F 9/007* (2006.01)
*A61B 17/00* (2006.01)

(52) U.S. Cl.
CPC .......... *A61B 18/00* (2013.01); *A61F 9/00745* (2013.01); *A61B 2017/0015* (2013.01); *A61B 2017/00146* (2013.01)

(58) Field of Classification Search
CPC .......... A61B 18/00; A61B 2017/00146; A61B 2017/0015; A61F 9/00745; A61F 9/00736
USPC .......................................... 606/107
See application file for complete search history.

(56) References Cited

U.S. PATENT DOCUMENTS

| 5,591,127 A | * | 1/1997 | Barwick, Jr. ....... A61F 9/00745 604/66 |
| 5,630,420 A | * | 5/1997 | Vaitekunas .... A61B 17/320068 600/459 |
| 6,884,252 B1 | * | 4/2005 | Urich .................. A61F 9/00745 604/22 |
| 6,997,935 B2 | | 2/2006 | Anderson et al. |

(Continued)

FOREIGN PATENT DOCUMENTS

WO WO 2010/054144 A2 5/2010

OTHER PUBLICATIONS

International Search Report dated Nov. 29, 2012 of international application PCT/EP2012/068767 on which this application is based.

(Continued)

*Primary Examiner* — Tan-Uyen T Ho
*Assistant Examiner* — Erich G Herbermann
(74) *Attorney, Agent, or Firm* — Walter Ottesen, P.A.

(57) ABSTRACT

An ophthalmic surgical control apparatus is configured to be connectable to a piezo handpiece for emulsifying an eye lens. The control apparatus includes a frequency generator having a first and a second frequency module. The first frequency module generates a first oscillation signal having a first frequency lower than the ultrasonic resonant frequency of the piezo handpiece. The second frequency module generates a second oscillation signal having a second frequency greater than the ultrasonic resonant frequency of the piezo handpiece. A frequency generator control module controls the first and the second frequency modules.

7 Claims, 7 Drawing Sheets

(56) References Cited

U.S. PATENT DOCUMENTS

| | | |
|---|---|---|
| 8,303,530 B2 | 11/2012 | Injev et al. |
| 2001/0025184 A1 | 9/2001 | Messerly |
| 2007/0249942 A1 | 10/2007 | Salehi et al. |
| 2012/0065578 A1* | 3/2012 | Zhou .................. A61M 1/0064 604/22 |

OTHER PUBLICATIONS

English translation and German Office action dated Dec. 8, 2011 of German patent application 10 2011 114 584.6 on which the claim of priority is based.

* cited by examiner

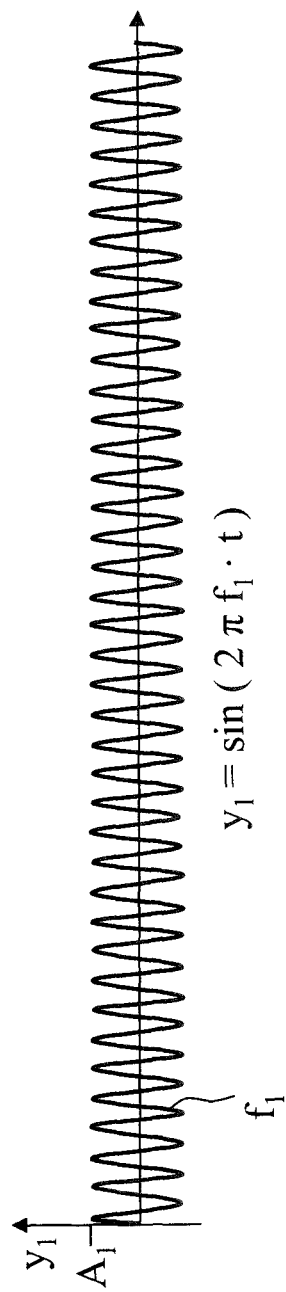
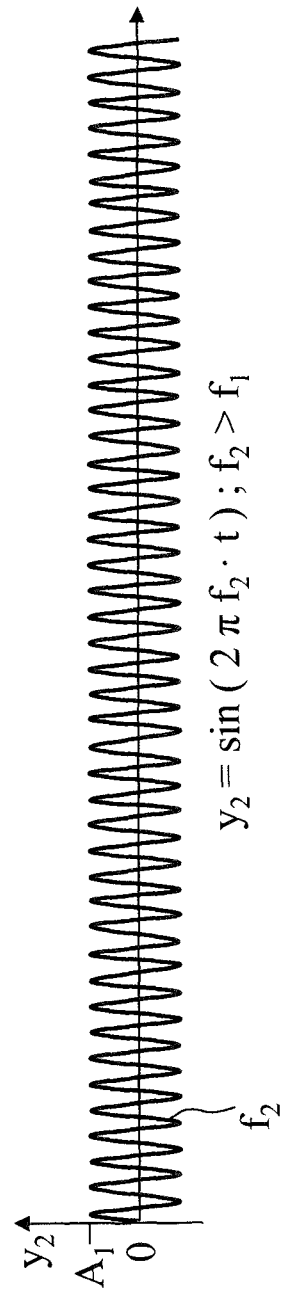
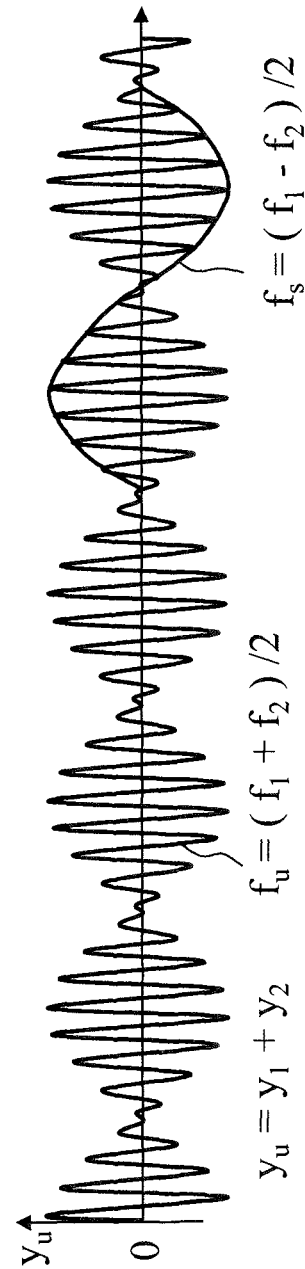

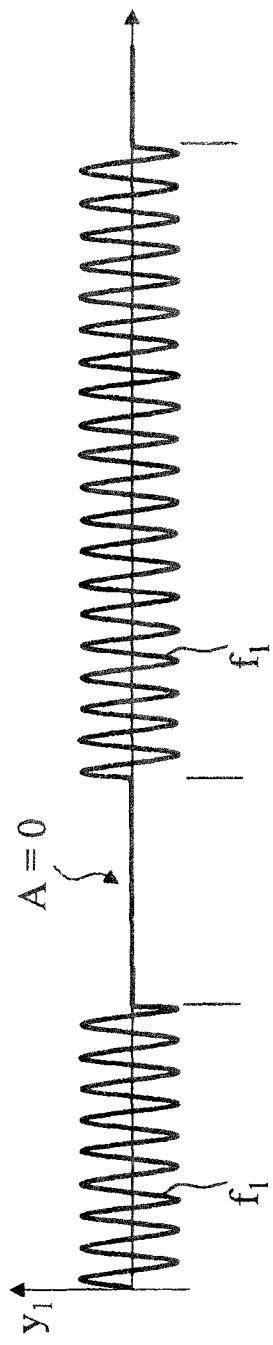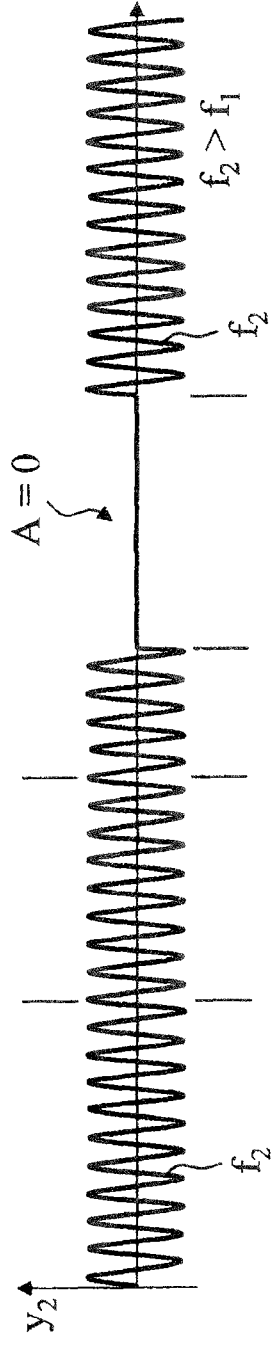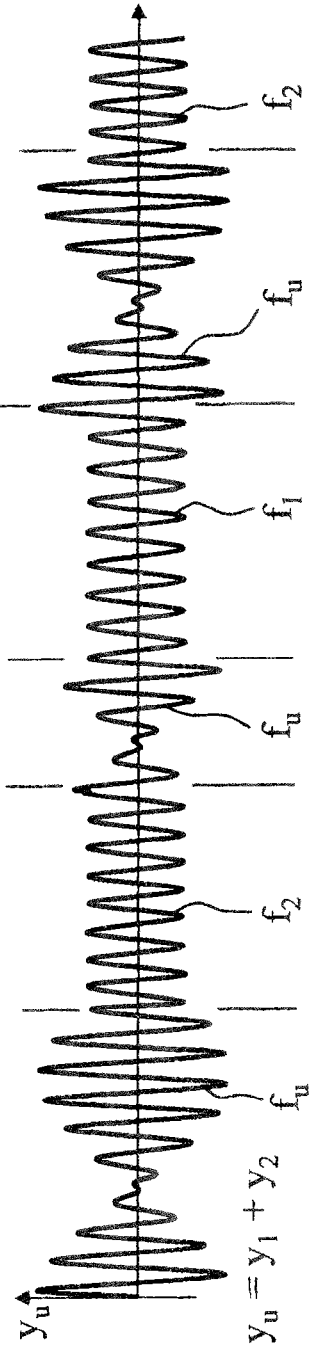

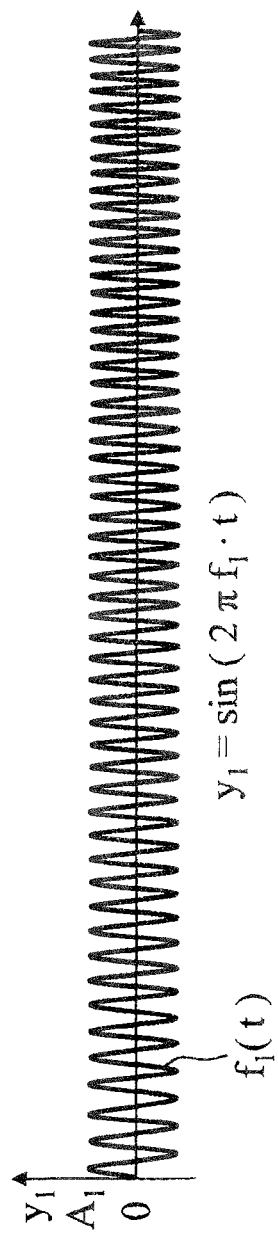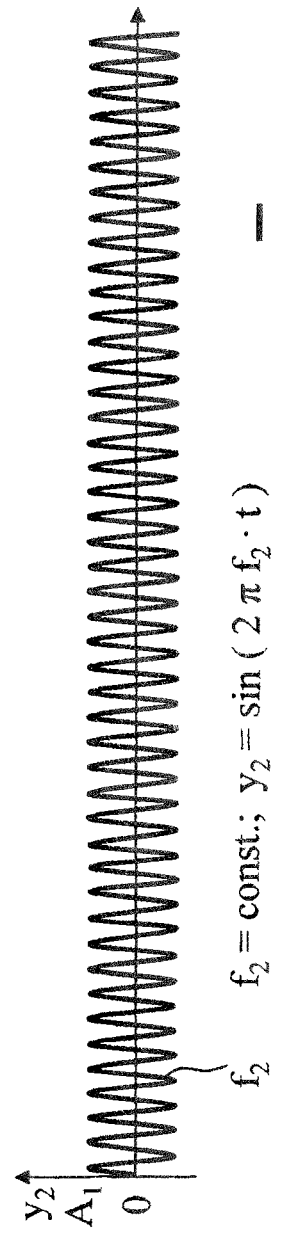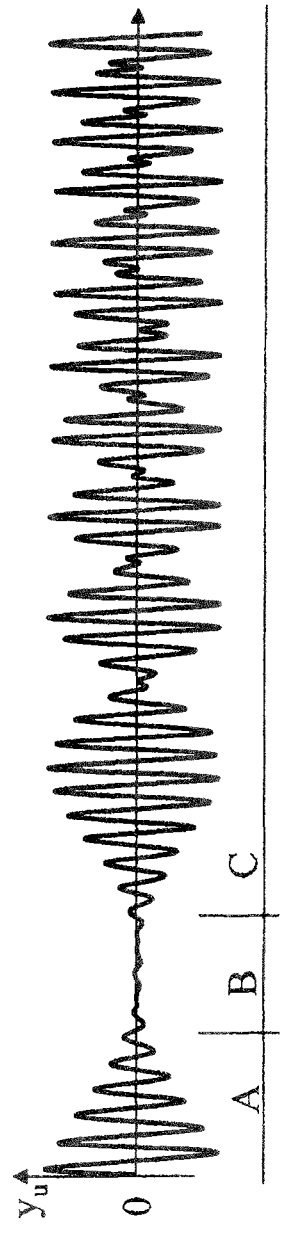

OPHTHALMIC SURGICAL CONTROL APPARATUS

CROSS REFERENCE TO RELATED APPLICATIONS

This application is a continuation application of international patent application PCT/EP2012/068767, filed Sep. 24, 2012, designating the United States and claiming priority from German application 10 2011 114 584.6, filed Sep. 30, 2011, and the entire content of both applications is incorporated herein by reference.

FIELD OF THE INVENTION

The invention relates to an ophthalmic surgical control apparatus and an ophthalmic surgical system including such a control apparatus.

BACKGROUND OF THE INVENTION

There are a number of surgical techniques for treating a clouding of the lens, which is referred to as a cataract in medicine. The most common technique is phacoemulsification. Here, a hollow needle vibrating in the ultrasonic range and including a cutting edge at its front end is used to shatter (emulsify) the clouded eye lens into such small pieces that these pieces can be suctioned away through the hollow needle. Subsequently, the surgeon inserts an artificial lens as a replacement for the lens shattered in this way. An essential component when carrying out such phacoemulsification is a handpiece including the aforementioned hollow needle. The required ultrasonic vibrations for shattering the clouded eye lens can be produced in such a way that the handpiece is provided with piezoceramic elements. If a voltage is applied to these piezoceramic elements, a change in length can be caused due to the piezoelectric effect, and so a needle connected to the piezoceramic elements can be deflected in the longitudinal direction.

In order to achieve complete emulsification of the eye lens and hence a high effectiveness in the shortest possible time, it is useful to move the hollow needle with the largest possible amplitudes. This can be performed in such a way that the piezoelectric elements are operated in the region of the resonant frequency of the handpiece. In the unloaded state, the resonant frequency of a handpiece with a hollow needle can be determined very precisely. However, as soon as the needle comes into contact with the lens to be emulsified, the mass conditions change and so there is a shift in the resonant frequency. In order to respectively operate such a handpiece in the region of the resonant frequency where possible, U.S. Pat. No. 6,997,935 B2 proposes to detect the phase between the applied voltage and the flowing current for operating the piezoelectric elements and to regulate it in such a way that, in accordance with the equation $P = U \cdot I \cdot \cos \varphi$, a power which is as close to the maximum as possible is achieved. So that the factor $\cos \varphi$ assumes a value that is as large as possible, $\cos \varphi = 1$ or $\varphi = 0$ must apply. Such a situation is given in the case of resonance. However, if there is a shift in the resonant frequency, for example due to change in the mechanical load on the cutting tip, the phase angle $\varphi$ no longer equals 0, but rather lies in the range between 0 and $-\pi/2$ or 0 and $+\pi/2$. In accordance with U.S. Pat. No. 6,997,935 B2, after detecting the phase angle $\varphi$, the excitation frequency is regulated in such a way that the excitation frequency of the cutting tip corresponds to the natural frequency $\omega_0$.

A cause for the shift in the resonant frequency lies not only in a modified load due to the lens fragments (change in mass) but also in the heating of the handpiece during relatively long operation and in aging of the piezoceramic elements and hence changes in the physical properties thereof. These parameters can superpose arbitrarily. A disadvantage of this is that there has to be constant updating so that the piezoceramic elements vibrate precisely at their resonant frequency. A further disadvantage lies in the fact that a plurality of successive measurement points of the voltage and current profile always have to be detected over time in order to determine the phase angle. This causes relatively slow regulation. Consequently, the handpiece does not really vibrate at its resonant frequency despite such large metrological and regulatory outlay. Rather, there always is a significant time delay in the adaptation to the respective current resonant frequency due to the slow regulation.

If the piezoceramic elements of the handpiece are actuated for a relatively long time during a phacoemulsification, there is heating not only of the piezoceramic elements, but, in the case of a sufficiently long operation, the surroundings of the hollow needle actuated by the piezoceramics are also heated to such an extent that the cornea, which is pierced for phacoemulsification, can burn in the vicinity of the needle. Since such injury must be avoided at all costs, it is conventional for the operation of the piezoceramic elements to be interrupted for a predetermined period of time. In the operating breaks created thus, no ultrasound energy is supplied to the piezoceramic elements, and so the hollow needle and its surroundings can cool down. A disadvantage here is that there needs to be relatively complicated actuation of the piezoceramic elements so that these can be in a vibrating state or in a pause state during predetermined periods of time.

SUMMARY OF THE INVENTION

It is an object of the invention to provide an ophthalmic surgical control apparatus and a system including such a control apparatus, via which the emulsification of an eye lens can be achieved in a short time with great effectiveness but nevertheless low control complexity.

The object is achieved by an ophthalmic surgical control apparatus having a frequency generator, wherein the frequency generator includes:

a first frequency module configured to produce a first vibration signal at a first frequency, wherein the first frequency is lower than an ultrasonic resonant frequency of an ophthalmic surgical piezo handpiece, for emulsifying an eye lens, that can be connected to the control device, and a second frequency module configured to produce a second vibration signal at a second frequency, wherein the second frequency is higher than the ultrasonic resonant frequency of the ophthalmic surgical piezo handpiece that can be connected to the control device, wherein the control device includes a frequency generator control module for actuating the first frequency module and the second frequency module.

Using such a control apparatus, it is possible to produce a first vibration signal at a first frequency and a second vibration signal at a second frequency, wherein the first frequency does not equal the second frequency. If both frequencies are combined with one another, for example by additive superposition, it is possible to produce a beat frequency. The continuously changing amplitude is characteristic for such a beat frequency. If the first vibration signal and the second vibration signal have an amplitude with the same absolute value, an addition of the two vibration signals leads to the absolute values of the amplitudes to add to zero at regular intervals.

The amplitude of the beat vibration changes with a frequency in accordance with the following equation:

$$f_S = (f_1 - f_2)/2$$

where $f_1$ is the first frequency of the first vibration signal and $f_2$ is the second frequency of the second vibration signal. As a result of the absolute values of the beat vibration regularly adding to zero, the hollow needle rests at these moments and does not introduce any energy into the eye. If the hollow needle is operated with such a beat vibration, there is a regular interruption of the energy supplied to the eye without any further control.

Reference is made to the fact that it is not the overriding goal to achieve a complete interruption of vibrations, during which the amplitude of the vibration has an absolute value of zero. Rather, the goal is to repeatedly provide periods of time during phacoemulsification, during which the eye can cool down. This is also achieved if only a little amount of energy is supplied to the eye in predetermined periods of time. Such a situation occurs in the case of a vibration having a relatively low amplitude. Depending on the selection of the two vibration frequencies, this therefore results in periods of time with a predetermined length during which the amplitude still is relatively low.

Reference is further made to the fact that, within the scope of this document, the ultrasonic resonant frequency of the piezo handpiece is not intended to mean only the resonant frequency of the handpiece on its own, that is with a housing, piezo stacks and a hollow needle coupled therewith, as well as electrical connection elements within the housing, but, in addition to the aforementioned components, this should also include, for example, a transformer, electric filters and other electric components required for the ultrasonic resonant circuit, since it is only all components together that determine the ultrasonic resonant frequency of the piezo handpiece.

The first vibration signal can be impressed upon a first stack of piezoceramic elements in the piezo handpiece, while the second vibration signal can be impressed upon a second stack of piezoceramic elements, placed therebehind, of the piezo handpiece. The piezoceramic elements are therefore connected mechanically in series, and so the vibration signals can superpose in an additive manner. Thus, when using the control apparatus according to the invention, there is no need anymore for an active periodic interruption of the vibration signal to be undertaken, as is still conventional in solutions according to the prior art. Rather, in the case of an additive superposition of both vibration signals, a regular interruption sets in automatically.

A further advantage of this embodiment lies in the fact that, for operating a piezo handpiece with a first stack and a second stack, the control apparatus can be provided with two amplifiers which, compared to conventional amplifiers for operating a piezo handpiece, only need to have half of the power. This reduces the complexity for operating the piezo handpiece.

Moreover, by an appropriate skillful selection of the first frequency and/or the second frequency, it is possible to achieve the operation of the piezo handpiece at the resonant frequency or near the resonant frequency. Thus, the invention deliberately dispenses with undertaking a complicated measurement of the voltage and current profile over time and carrying out a corresponding evaluation by establishing the phase angle and thereupon updating this appropriately with delay. Rather, there is no regulation in the direction of a resonant frequency. It was found that skillful selection of the first frequency and second frequency allows an operation of the piezo handpiece sufficiently close to the current resonant frequency.

In accordance with a preferred embodiment, the control apparatus includes a superposition module configured to superpose, in an additive manner, the first vibration signal and the second vibration signal and to provide this as superposition vibration signal for operating the piezo handpiece. This renders it possible to provide the superposition vibration signal as only vibration signal to a piezo handpiece by the control apparatus. This renders it possible for every previously known piezo handpiece to be able to be connected to such a control apparatus.

Furthermore, it is possible for the control apparatus to be configured to provide the first vibration signal and/or the second vibration signal simultaneously only during a predetermined period of time. This allows operation at a first frequency, with a beat frequency also being present at times, so that, overall, a very variable frequency of the piezo handpiece with very variable amplitude is present. The advantage lies in the fact that fragments of an eye lens with different degrees of hardness and different sizes can be reliably shattered. The variability in frequency and amplitude leads to the introduction of energy with very different magnitudes.

Preferably, the first vibration signal has a first amplitude and the second vibration signal has a second amplitude, wherein the first amplitude is higher than the second amplitude or the second amplitude is higher than the first amplitude. This produces a so-called impure beat, in which there is no resultant amplitude of the overall vibration that adds to zero. This can also lead to a large variation in the supplied energy, and so there is a higher probability of fragments with different degrees of hardness and different sizes being able to be shattered reliably and in a short time.

In accordance with a preferred embodiment, the first frequency and the second frequency vary in time by a predetermined absolute value. When adding the corresponding vibration signals with such a first frequency and second frequency, there is no constant beat frequency, but rather a vibration with varying frequency. The frequency varies by half the absolute value such that, in the case of a large enough absolute value, the hollow needle of the handpiece can repeatedly vibrate at the resonant frequency of the handpiece, without it being necessary to precisely measure or set the resonant frequency. This allows a very good effectiveness to be achieved. Furthermore, by adding the two vibration signals, the above-described effect, namely that the amplitudes add to zero at regular intervals, occurs, and so no active interruption of the vibration signals is required.

The object is also achieved by an ophthalmic surgical system with an ophthalmic surgical control apparatus as described above, wherein the system furthermore includes a piezo handpiece, a fluid control device, a power supply unit and an input unit, wherein these components together are coupled to a central control unit.

BRIEF DESCRIPTION OF THE DRAWINGS

The invention will now be described with reference to the drawings wherein:

FIGS. 3A to 3C show a schematic view of a first vibration signal, a second vibration signal and an associated beat vibration signal;

FIGS. 4A to 4C show a further schematic view with a first vibration signal and a second vibration signal and an associated beat vibration signal;

FIGS. 6A to 6C show a further view of a first vibration signal and a second vibration signal and an associated beat vibration signal;

DESCRIPTION OF THE PREFERRED
EMBODIMENTS OF THE INVENTION

Figure 1:
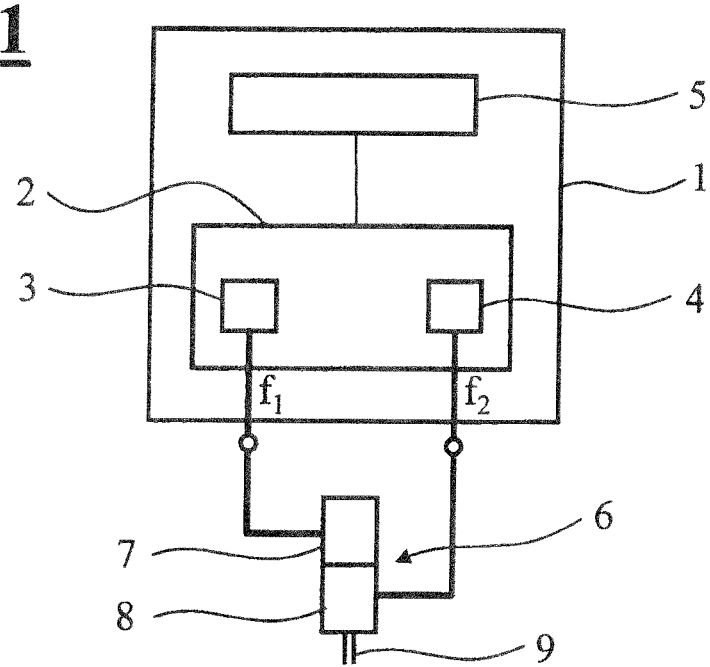
FIG. 1 is a schematic view of a first embodiment of an ophthalmic surgical control apparatus in accordance with the invention.

FIG. 1 shows an ophthalmic surgical control apparatus 1 in accordance with the invention. The control apparatus includes an ophthalmic surgical frequency generator 2 with a first frequency module 3 and a second frequency module 4. The first frequency module 3 is configured to produce a first vibration signal at a first frequency $f_1$, with the second frequency module 4 being configured to produce a second vibration signal at a second frequency $f_2$. The ophthalmic surgical frequency generator 2 is actuated via a frequency generator control module 5.

In this embodiment of the control apparatus 1, the first vibration signal at the first frequency $f_1$ and the second vibration signal at the second frequency $f_2$ are provided at the output of the control apparatus. Both vibration signals can be supplied to a piezo handpiece 6, wherein the first vibration signal can be supplied to a first piezo stack 7 and the second vibration signal can be supplied to a second piezo stack 8. Both piezo stacks are arranged in series such that the signals can superpose in an additive manner. This renders it possible to produce a beat frequency from both vibration signals, and so the hollow needle 9 of the piezo handpiece 6 can vibrate at a beat frequency.

Figure 2:
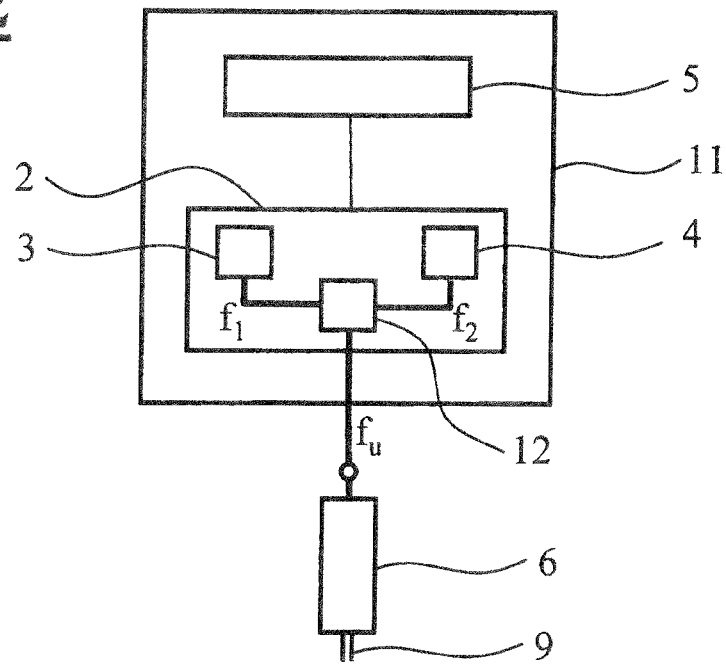
FIG. 2 is a schematic view of a second embodiment of the ophthalmic surgical control apparatus in accordance with the invention.

FIG. 2 shows a second embodiment of an ophthalmic surgical control apparatus 11, wherein the control apparatus includes an ophthalmic surgical frequency generator 2 with a first frequency module 3 and a second frequency module 4. Like in the first embodiment of the ophthalmic surgical control apparatus 1, the first frequency module 3 can emit a first vibration signal at a first frequency $f_1$ and the second frequency module 4 can emit a second vibration signal at a second frequency $f_2$. However, in this second embodiment of the ophthalmic surgical control apparatus 11, both vibration signals are supplied to a superposition module 12, which is configured to superpose the first vibration signal at the first frequency $f_1$ and the second vibration signal at the second frequency $f_2$ in an additive manner and provide this as superposition vibration signal at a frequency $f_u$ at the output of the control apparatus 11. This superposition vibration signal can then be supplied to a piezo handpiece 6, wherein this piezo handpiece only requires a single connector for operating all piezo stacks within the piezo handpiece.

An advantage of this embodiment lies in the fact that every conventional piezo handpiece with only one connector can be employed.

FIG. 3A shows a schematic view of a first vibration signal at a first frequency $f_1$ with an amplitude A=1. The first vibration signal is a sinusoidal vibration in accordance with the equation $y_1=\sin(2\pi f_1 \cdot t)$. Furthermore, FIG. 3B shows a second vibration signal at a second frequency $f_2$ with an amplitude A=1. The second vibration signal is a sinusoidal vibration in accordance with the equation $y_2=\sin(2\pi f_2 \cdot t)$, where $f_2$ does not equal $f_1$. If both vibration signals are superposed, this results in a superposition vibration signal in accordance with the equation $y_u=y_1+y_2$, see FIG. 3C, wherein the superposition vibration signal has a superposition frequency $f_u=(f_1+f_2)/2$ with an amplitude frequency $f_S=(f_1-f_2)/2$.

FIG. 4A shows a further view of a first vibration signal at a first frequency $f_1$; FIG. 4B shows a second vibration signal at a second frequency $f_2$. In contrast to the vibration signals depicted in FIG. 3A and FIG. 3B, the first vibration signal in accordance with FIG. 4A has an amplitude A=0 for a predetermined period of time. The second vibration signal at a frequency $f_2$ likewise has a period of time during which the amplitude A=0, see FIG. 4B. In the case of a superposition of the two vibration signals, a beat vibration signal with different frequencies emerges, see FIG. 4C. In the embodiment depicted in FIG. 4C, a superposition frequency $f_u$ occurs first, followed by the second frequency $f_2$, then followed again by the superposition frequency $f_u$, then followed by the frequency $f_1$, then followed by the superposition frequency $f_u$ and then followed again by the second frequency $f_2$. It can clearly be seen that this results in a vibration with strongly varying amplitude and varying frequencies, and so there is a high probability that lens fragments with different degrees of hardness and different sizes can be shattered reliably and within a short period of time.

Figure 5A:
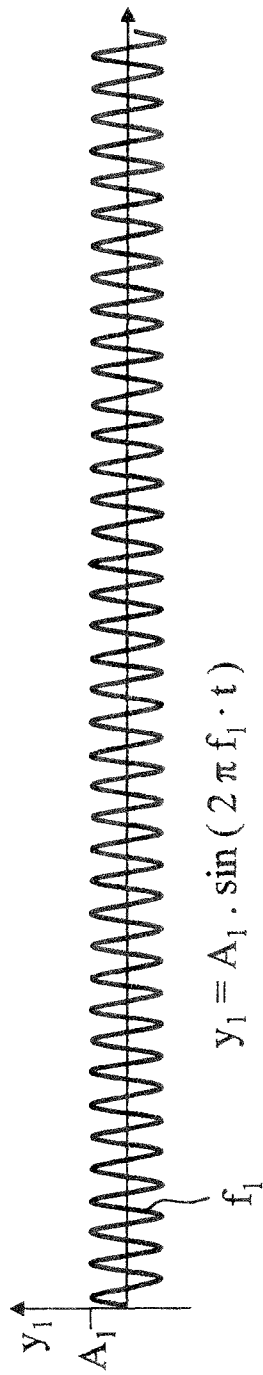
FIGS. 5A to 5C show a further view of a first vibration signal and a second vibration signal and an associated beat vibration signal.
Figure 5B:
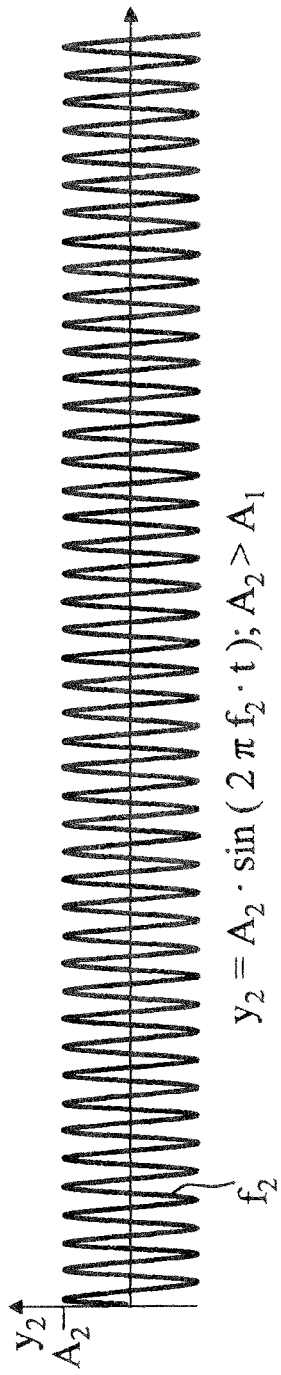
Figure 5C:
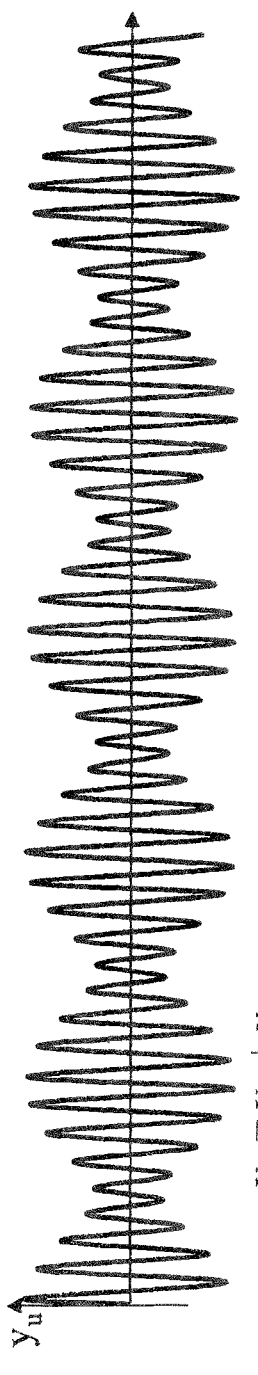

FIG. 5A shows a further view of a first vibration signal at a first frequency $f_1$ and with an amplitude $A_1$. FIG. 5B shows a second vibration signal at a second frequency $f_2$ and with a second amplitude $A_2$, wherein $f_1$ does not equal $f_2$ and $A_1$ does not equal $A_2$. In the case of an additive superposition of both vibration signals, a superposition vibration signal results, see FIG. 5C, in which there is no amplitude of the vibration adding up to zero. By skillful selection of the amplitudes $A_1$ and $A_2$ and frequencies $f_1$ and $f_2$, it is possible to produce a superposition vibration signal which provides sufficient energy for shattering lens particles with different sizes and different degrees of hardness but also has sufficient periods of time in which the energy is so low that excessively strong heating of the eye can be prevented.

FIG. 6A shows a further view with a first vibration signal at a first frequency and FIG. 6B shows a second vibration signal at a second frequency, which lies above the resonant frequency. The first vibration signal has a frequency $f_1$, which varies in time and is not constant. The second vibration signal has a frequency $f_2$, which is constant. The result of the additive superposition of both vibration signals is a superposition vibration signal at a superposition frequency, see FIG. 6C. In the region "A", $f_2$ is greater than $f_1(t)$, and so a superposition frequency is produced, which is less than the resonant frequency of the piezo handpiece. In the region "B", $f_1$ is approximately equal to $f_2$, with the vibrations being phase shifted by almost 180 degrees. In the region "C", $f_1(t)$ is greater than $f_2$, and so the superposition frequency is greater than the resonant frequency of the piezo handpiece. In the region "A", there must be a zone in which the resonant frequency of the handpiece is reached precisely.

That is, the superposition frequency varies continuously so that the handpiece being operated precisely within the resonant frequency for a certain period of time is always ensured, even though no complicated measurement of a voltage and current profile within the piezo handpiece is required.

Figure 7A:
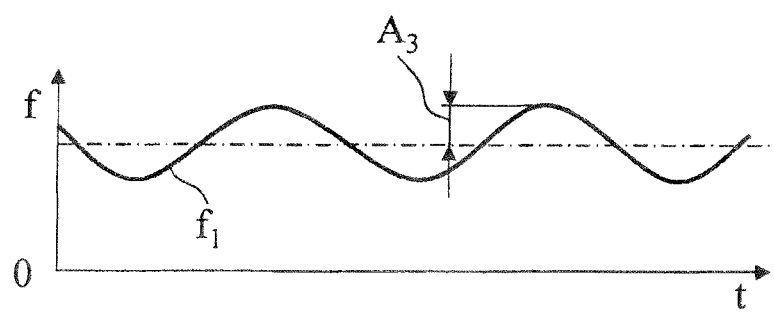
FIGS. 7A to 7C show a schematic view of the first vibration signal and of the second vibration signal and of the associated beat vibration signal in accordance with FIG. 6; and, FIG. 8 is a schematic view of the ophthalmic surgical system in accordance with the invention.
Figure 7B:
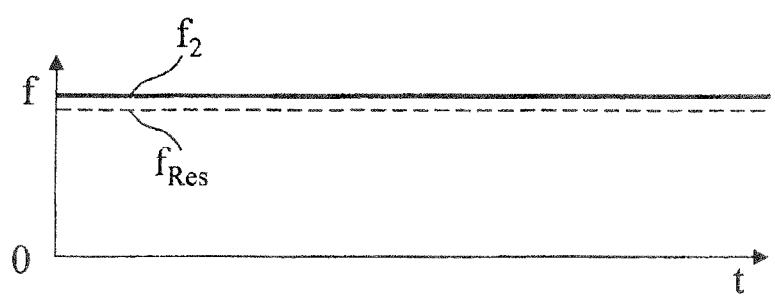
Figure 7C:
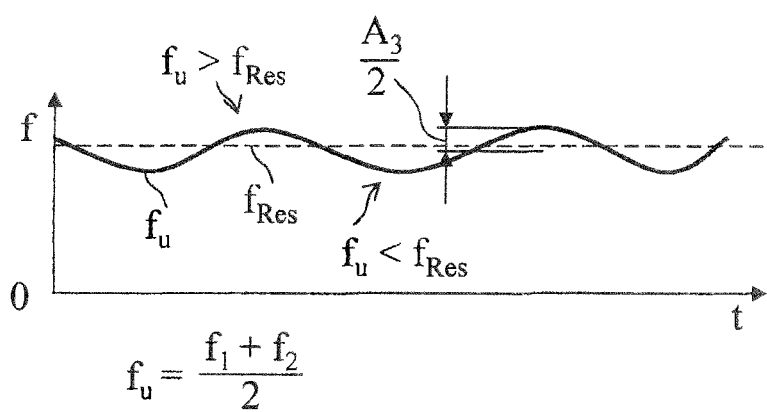

FIG. 7 explains this situation once again. The first vibration signal at the first frequency varies in sinusoidal fashion at a frequency $f_1(t)$ and at an amplitude $A_3$, see FIG. 7A. The second vibration signal has a constant frequency $f_2$, which is higher than the resonant frequency $f_{Res}$ of the piezo handpiece, see FIG. 7B. In the case of an additive superposition of the first vibration signal and the second vibration signal, the result is a superposition vibration signal at a frequency $f_u$, which likewise varies in sinusoidal fashion. In the case of an appropriate selection of the frequencies $f_1$ and $f_2$ and the amplitude $A_3$, it is possible for the superposition vibration signal to have a frequency which continuously varies about the resonant frequency of the piezo handpiece. As a result, there are regions in which the superposition vibration signal has a superposition frequency that is greater than the resonant frequency of the handpiece and regions in which it is less than the resonant frequency of the handpiece.

Figure 8:
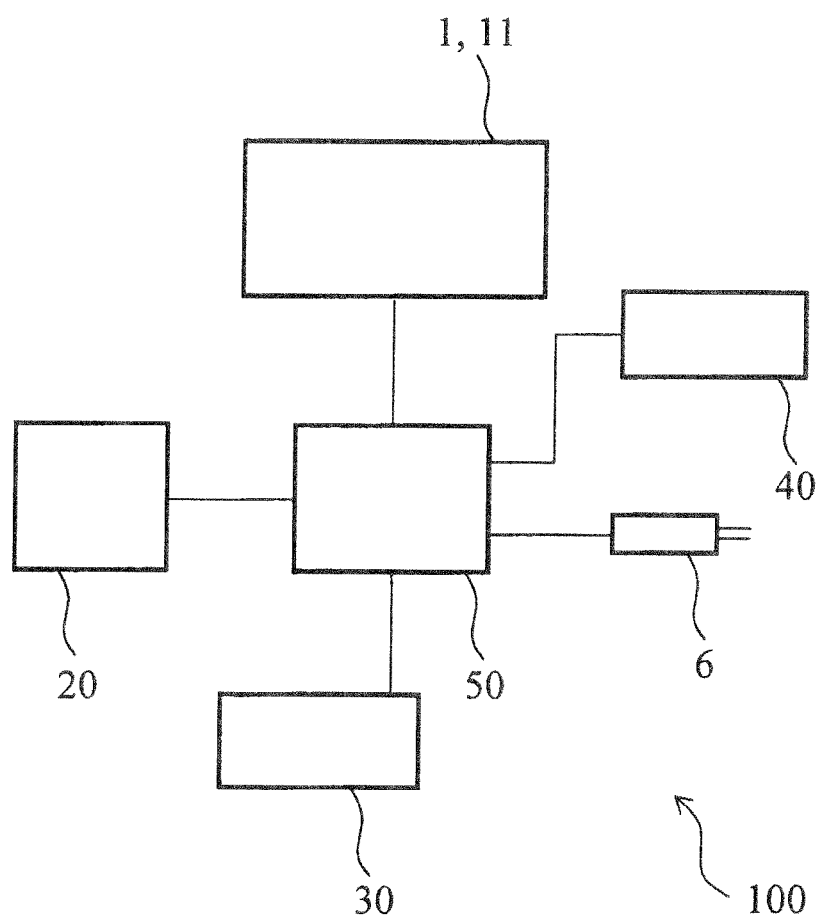

FIG. 8 shows a schematic view of the ophthalmic surgical system 100 in accordance with the invention, with the system including: an ophthalmic surgical control apparatus 1 or 11, a fluid control device 20, a power supply unit 30, an input unit 40, and a piezo handpiece 6, wherein these components together are coupled with a central control unit 50.

It is understood that the foregoing description is that of the preferred embodiments of the invention and that various changes and modifications may be made thereto without departing from the spirit and scope of the invention as defined in the appended claims.

What is claimed is:

1. An ophthalmic surgical control apparatus configured to be connectable to an ophthalmic surgical piezo handpiece for emulsifying an eye lens, the ophthalmic surgical piezo handpiece having a hollow needle defining a longitudinal axis and having an ultrasonic resonant frequency, the ophthalmic surgical control apparatus comprising: a frequency generator having a first and a second frequency module; said first frequency module being configured to generate a first oscillation signal having a first frequency $f_1$ and said first oscillation signal being a sinusoidal vibration in accordance with equation $y_1 = \sin(2\pi f_1 \times t)$; said first frequency being lower than the ultrasonic resonant frequency of the ophthalmic surgical piezo handpiece; said second frequency module being configured to generate a second oscillation signal having a second frequency $f_2$ and said second oscillation signal being a sinusoidal vibration in accordance with equation $y_2 = \sin(2\pi f_2 \times t)$; said second frequency being greater than the ultrasonic resonant frequency of the ophthalmic surgical piezo handpiece; a frequency generator control module configured to control said first and said second frequency modules; a superposition module configured to additively superpose said first oscillation signal and said second oscillation signal in accordance with equation $y_u = y_1 + y_2$ so as to generate a superposition oscillation signal having a superposition oscillation frequency; said superposition module being further configured to provide said superposition oscillation signal for operation of the ophthalmic surgical piezo handpiece; and, said ophthalmic surgical piezo handpiece containing a plurality of piezo stacks connected mechanically in series so as to permit an oscillation of said hollow needle only along said longitudinal axis.

2. The ophthalmic surgical control apparatus of claim 1, wherein the ophthalmic surgical control apparatus is further configured to provide one of said first oscillation signal and said second oscillation signal only for a predetermined time duration.

3. The ophthalmic surgical control apparatus of claim 1, wherein the ophthalmic surgical control apparatus is further configured to provide said first oscillation signal and said second oscillation signal simultaneously only for a predetermined amount of time.

4. The ophthalmic surgical control apparatus of claim 1, wherein:
said first oscillation signal has a first amplitude;
said second oscillation signal has a second amplitude; and,
said first oscillation signal is either higher than said second oscillation signal or is lower than said second oscillation signal.

5. The ophthalmic surgical control apparatus of claim 1, wherein at least one of said first frequency and said second frequency is varied over time by a predetermined amount.

6. An ophthalmic surgical system comprising: an ophthalmic surgical piezo handpiece for emulsifying an eye lens; said ophthalmic surgical piezo handpiece having a hollow needle defining a longitudinal axis and having an ultrasonic resonant frequency; a fluid control device; an energy supply; an input unit; and, an ophthalmic surgical control apparatus including a frequency generator having a first and a second frequency module; said first frequency module being configured to generate a first oscillation signal having a first frequency $f_1$ and said first oscillation signal being a sinusoidal vibration in accordance with equation $y_1 = \sin(2\pi f_1 \times t)$; said first frequency being lower than the ultrasonic resonant frequency of the ophthalmic surgical piezo handpiece; said second frequency module being configured to generate a second oscillation signal having a second frequency $f_2$ and said second oscillation signal being a sinusoidal vibration in accordance with equation $y_2 = \sin(2\pi f_2 \times t)$; said second frequency being greater than the ultrasonic resonant frequency of the ophthalmic surgical piezo handpiece; said ophthalmic surgical control apparatus further including a frequency generator control module configured to control said first and said second frequency modules; a central control unit coupled to said ophthalmic surgical piezo handpiece, said fluid control device, said energy supply, said input unit, and said ophthalmic surgical control apparatus; a superposition module configured to additively superpose said first oscillation signal and said second oscillation signal in accordance with equation $y_u = y_1 + y_2$ so as to generate a superposition oscillation signal having a superposition oscillation frequency; said superposition module being further configured to provide said superposition oscillation signal for operation of the ophthalmic surgical piezo handpiece; and, said ophthalmic surgical piezo handpiece containing a plurality of piezo stacks connected mechanically in series so as to permit an oscillation of said hollow needle only along said longitudinal axis.

7. An ophthalmic surgical control apparatus configured to be connectable to an ophthalmic surgical piezo handpiece for emulsifying an eye lens, the ophthalmic surgical piezo handpiece having a hollow needle defining a longitudinal axis and having an ultrasonic resonant frequency, the ophthalmic surgical control apparatus comprising: a frequency generator having a first and a second frequency module; said first frequency module being configured to generate a first oscillation signal having a first frequency; said first frequency being lower than the ultrasonic resonant frequency of the ophthalmic surgical piezo handpiece; said second frequency module being configured to generate a second oscillation signal having a second frequency; said second frequency being greater than the ultrasonic resonant frequency of the ophthalmic surgical piezo handpiece; a frequency generator control module configured to control said first and said second frequency modules; said ophthalmic surgical piezo handpiece having a first piezo stack connected to said first frequency module to receive said first oscillation signal and a second piezo stack connected to said second frequency module to receive said second oscillation signal; and, said first and second piezo stacks being arranged in series so as to cause said first and second signals to superpose in an additive manner to impart vibrations to said hollow needle only along said longitudinal axis at a beat frequency causing a regular interruption in said vibrations and so cause a regular interruption of energy supplied to the eye lens during a surgical procedure thereon.

\* \* \* \* \*